US010258632B2

(12) United States Patent
Gonzalez et al.

(10) Patent No.: US 10,258,632 B2
(45) Date of Patent: Apr. 16, 2019

(54) METHOD OF PREVENTION OF NEUROLOGICAL DISEASES

(71) Applicant: International Stem Cell Corporation, Carlsbad, CA (US)

(72) Inventors: Rodolfo Gonzalez, Carlsbad, CA (US); Ibon Garitaonandia, Carlsbad, CA (US); Russell A. Kern, Carlsbad, CA (US)

(73) Assignee: International Stem Cell Corporation, Carlsbad, CA (US)

( * ) Notice: Subject to any disclaimer, the term of this patent is extended or adjusted under 35 U.S.C. 154(b) by 0 days.

(21) Appl. No.: 14/397,981

(22) PCT Filed: Jun. 3, 2013

(86) PCT No.: PCT/US2013/043927
§ 371 (c)(1),
(2) Date: Oct. 30, 2014

(87) PCT Pub. No.: WO2013/184591
PCT Pub. Date: Dec. 12, 2013

(65) Prior Publication Data
US 2015/0094289 A1    Apr. 2, 2015

Related U.S. Application Data

(60) Provisional application No. 61/655,742, filed on Jun. 5, 2012.

(51) Int. Cl.
*A61K 31/57* (2006.01)
*A61K 31/47* (2006.01)
*A61K 31/55* (2006.01)

(52) U.S. Cl.
CPC ............. *A61K 31/57* (2013.01); *A61K 31/47* (2013.01); *A61K 31/55* (2013.01)

(58) Field of Classification Search
CPC ......... A61K 31/47; A61K 31/57; A61K 31/55
USPC ................................... 514/177, 212.06, 312
See application file for complete search history.

(56) References Cited

U.S. PATENT DOCUMENTS

| | | | |
|---|---|---|---|
| 2004/0198753 A1* | 10/2004 | Kase et al. ................ | 514/263.2 |
| 2009/0226536 A1 | 9/2009 | Arenas et al. | |
| 2009/0291134 A1 | 11/2009 | Ahmad et al. | |
| 2011/0312894 A1 | 12/2011 | Wu | |

FOREIGN PATENT DOCUMENTS

EP    1 224 938 A1    7/2002

OTHER PUBLICATIONS

Lee et al. Kynurenic acid attenuates MPP+ induced dopaminergic neuronal cell death via a Bax-mediated mitochondrial pathway. European Journal of Cell Biology 87 (2008) pp. 389-397.*
Jorda et al. Evaluation of the neuronal apoptotic pathways involved in cytoskeletal disruption-induced apoptosis. Biochemical Pharmacoloy 70 (2005) 470-480.*
Castelo-Branco, G. et al.: "*GSK-3beta inhibition/beta-catenin stabilization in ventral midbrain precursors increases differentiation into dopamine neurons*", Journal of Cell Science, Cambridge University Press, Nov. 15, 2004, vol. 117, No. 24, pp. 5731-573.7.
Gaur et al.: "*Gugulipid, a new hypolipidemic agent, in patients of acute ischemic stroke: effect on clinical outcome, platelet function and serum lipids*"; Indian Journal of Pharmacology, Aug. 24, 1998, vol. 12, No. 3/04, pp. 65-69.
Supplementary European Search Report dated Sep. 10, 2015 regarding EP 13 80 0837.
Saxena, G. et al.: "*Gugulipid, an extract of Commiphora whighitii with lipid-lowering properties, has protective effects against streptozotocin-induced memory deficits in mice*";. Pharmacology Biochemistry and Behavior, Apr. 3, 2007, vol. 86, No. 4, pp. 797-805.
Singapore Search Report dated Mar. 30, 2016, regarding SG 11201407412Q.
Nemeth, H. et al.: "*Kynurenines, Parkinson's disease and other neurodegenerative disorders: preclinical and clinical studies*"; J Neural Transm Suppl., 2006; (70): 285-304. (Abstract).
Russian Office Action dated Jun. 14, 2017, regarding RU 2014153894.
Chinese Office Action dated Jan. 16, 2017, regarding CN 201380026036.0.
Meselhy, Meselhy R.: "*Inhibition of LPS-induced NO production by the oleogum resin of Commiphora wightii and its constituents*"; Phytochemistry, 62, 2003, 213-218.
European Exam Report dated Jul. 2, 2018, regarding EP 13 800 837.0.
Adams, J. D. et al.: "*Effects of guggul in a rat model of stroke*"; Alternative Therapies in Health and Medicine, Jan. 1, 2001, vol. 8. No. 4, pp. 20-21, XP55209706.

* cited by examiner

*Primary Examiner* — Jennifer M Kim
(74) *Attorney, Agent, or Firm* — DLA Piper LLP (US)

(57) ABSTRACT

Provided herein are small molecules that have a neuroprotective or modulatory effect in the nervous system. The small molecules provided herein modulate dopaminergic neuronal activity. Also provided herein are methods of for the prophylaxis of or preventing the progression of Parkinson's Disease (PD).

13 Claims, No Drawings

METHOD OF PREVENTION OF NEUROLOGICAL DISEASES

CROSS-REFERENCE TO RELATED APPLICATIONS

This application is a 35 USC § 371 National Stage application of International Application No. PCT/US2013/043927 filed Jun. 3, 2013, now pending; which claims the benefit under 35 USC § 119(e) to U.S. Application Ser. No. 61/655,742 filed Jun. 5, 2012. The disclosure of each of the prior applications is considered part of and is incorporated by reference in the disclosure of this application.

BACKGROUND OF THE INVENTION

Field of the Invention

The present invention relates generally to small molecules for the treatment of neurological disorders and, more specifically, to methods for the prevention of Parkinson's Disease (PD) or preventing its progression in a subject with PD.

Background Information

Parkinson's disease is a common neurodegenerative disorder characterized clinically by bradykinesia, rigidity, tremor, and gait dysfunction, and pathologically by degeneration of dopamine neurons in the substantia nigra pars compacta (SNc) and projecting to the striatum (including the putamen).

There is no known cure for PD. Patients are treated with drugs and physical therapy to control the symptoms, but the disease is a progressive disorder and symptoms continue to worsen throughout life. There are four major categories of drugs used to treat PD: Levodopa, direct dopamine agonists, catechol-O-methyltransferase (COMT) inhibitors and anticholinergics. Other types of drugs include selegiline (an MAO-B inhibitor), amantadine (an antiviral agent), vitamin E and hormone replacement therapy. Although these treatments may provide some relief from the symptoms of PD, these noncurative drug treatments are often are accompanied by side effects, such as low blood pressure, nausea, constipation, and various psychiatric or behavioral disorders (e.g., hallucinations, depression, and sleep disorders). Present therapies provide satisfactory disease control for most patients, particularly in the early stages. However, no treatments protect against the continued degeneration of these neurons and, over time, all therapies fail. Chronic levodopa treatment is associated with motor complications, does not control potentially disabling features such as falling and dementia, and fails to prevent disease progression. (Olanow et al., *Neurology* 72: suppl 4:S1-S136 (2009)). Thus, many patients suffer disability despite available medical and surgical treatments. More effective treatments that improve clinical disease control and slow progression are urgently needed.

SUMMARY OF THE INVENTION

The present invention is based on the seminal discovery that guggulsterone, kynurenic acid, and kenpaullone may be use to modulate dopaminergic neuronal activity. Kenpaullone, through inhibition of GSK-3β, may have a protective effect in the nervous system against neurodegenerative disease and as such, may prevent apoptosis or degeneration of neurons. Additionally, guggulsterone, an inducible nitric oxide synthase (iNOS) inhibitor, may decrease the presence of nitric oxide (NO) in an ischemic area of the CNS, thereby decreasing the risk of toxic effects caused by NO.

Provided herein is a method for the prevention of Parkinson's Disease (PD). The method includes administering to a subject in need thereof a therapeutically effective amount of at least one of guggulsterone, kynurenic acid, or kenpaullone, or a pharmaceutically acceptable salt thereof.

Also provided herein is a method for preventing the progression of PD. The method includes administering to a subject in need thereof a therapeutically effective amount of at least one of guggulsterone, kynurenic acid, or kenpaullone, or a pharmaceutically acceptable salt thereof.

In certain aspects, guggulsterone, kynurenic acid, or kenpaullone are administered orally or by injection. By way of example, guggulsterone may be administered intravenously.

A method for modulating dopaminergic neuronal activity is provided. The method includes contacting dopaminergic neurons with at least one of guggulsterone, kynurenic acid, or kenpaullone, thereby modulating dopaminergic neuronal activity. In certain aspects, the dopaminergic neuronal activity is promoted or increased. Examples of dopaminergic neuronal activity include, but are not limited to, neuron function, neuron survival, or neurite outgrowth. In one aspect, dopamine release is increased or stimulated.

In certain aspects, guggulsterone, kynurenic acid, or kenpaullone may have a neuroprotective effect in the nervous system against neurodegenerative disease, such as PD.

In certain aspects, the E-isomer of guggulsterone (E-guggulsterone) is used for the methods described herein. In other aspects, the Z-isomer of guggulsterone (Z-guggulsterone) is used for the methods described herein. In yet other aspects, a mixture of both the E- and Z-isomers is used for the methods described herein.

In certain embodiments of the above aspects, the method includes administering, to a subject in need thereof, a therapeutically effective amount of at least one of guggulsterone, kynurenic acid, or kenpaullone, or a pharmaceutically acceptable salt thereof, in combination with a second form of therapy. In certain embodiments, the second form of therapy is an agent for treating Parkinson's Disease and may include, but is not limited to, levodopa, carbidopa, Sinemet, dopamine agonists (e.g., Requip, Mirapex, Neupro, Symmetrel), anticholinegics (e.g., Artane, Cogentin), Eldepryl, Azilect, and COMT inhibitors (e.g., Tasmar, Comtan). In other embodiments, the second form of therapy is an agent for treating Alzheimer's Disease and may include, but is not limited to donepezil, galantamine, memantine, rivastigmine, and tacrine.

DETAILED DESCRIPTION OF THE INVENTION

The following terms, definitions and abbreviations apply. Abbreviations used herein have their conventional meaning within the chemical and biological arts.

The term "patient" refers to organisms to be treated by the methods of the disclosure. Such organisms include, but are not limited to, humans. In the context of the disclosure, the term "subject" generally refers to an individual who will receive or who has received treatment described below (e.g., administration of the compounds of the disclosure, and optionally one or more additional therapeutic agents).

The disclosure also provides pharmaceutical compositions comprising at least one compound in an amount effective for treating a disorder, and a pharmaceutically acceptable vehicle or diluent. The compositions of the disclosure may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the disclosure may be formulated into therapeutic compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure include amine salts formed by the protonation of an amino group with inorganic acids such as hydrochloric acid, hydrobromic acid, hydroiodic acid, sulfuric acid, phosphoric acid, and the like. Salts of the disclosure may also include amine salts formed by the protonation of an amino group with suitable organic acids, such as p-toluenesulfonic acid, acetic acid, and the like. Additional excipients which are contemplated for use in the practice of the disclosure are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs, hydrates, and solvates of the compounds are included in the disclosure.

The disclosed pharmaceutical compositions may be administered by any suitable means, for example, orally, such as in the form of tablets, capsules, granules, syrups, elixirs, or powders; sublingually; buccally; parenterally, such as by subcutaneous, intravenous, intramuscular, intrathecal, or intracisternal injection or infusion techniques (e.g., as sterile injectable aqueous or non-aqueous solutions or suspensions); nasally such as by inhalation spray; topically, such as in the form of a drug-releasing skin patch, cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

The phrases "parenteral administration" and "administered parenterally" as used herein means modes of administration other than enteral and topical administration, usually by injection, and includes, without limitation, intravenous, intramuscular, intarterial, intrathecal, intracapsular, intraorbital, intracardiac, intradermal, intraperitoneal, transtracheal, subcutaneous, subcuticular, inimarticulare, subcapsular, subarachnoid, intraspinal and intrasternal injection and infusion.

In addition to primates, such as humans, a variety of other mammals can be treated according to the method of the disclosure. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The term "therapeutically effective amount" means the amount of the compound or pharmaceutical composition that will elicit the biological or medical response of a tissue, system, animal or human that is being sought by the researcher, veterinarian, medical doctor or other clinician, e.g., restoration or maintenance of vasculostasis or prevention of the compromise or loss or vasculostasis; reduction of tumor burden; reduction of morbidity and/or mortality.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the disclosure or pharmaceutical composition to the subject in need of treatment.

The pharmaceutical compositions for the administration of the compounds of this embodiment either alone or in combination with other agents, e.g., chemotherapeutic, may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Also useful as a solubilizer is polyethylene glycol, for example. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent or cosolvent or complexing agent or dispersing agent or excipient or combination thereof, for example 1,3-butane diol, polyethylene glycols, polypropylene glycols, ethanol or other alcohols, povidones, Tweens, sodium dodecyle sulfate, sodium deoxycholate, dimethylacetamide, polysorbates, poloxamers, cyclodextrins, e.g., sulfobutyl ether β-cyclodextrin, lipids, and excipients such as inorganic salts (e.g., sodium chloride), buffering agents (e.g., sodium citrate, sodium phosphate), and sugars (e.g., saccharose and dextrose). Among the acceptable vehicles and solvents that may be employed are water, dextrose solutions, Ringer's solutions and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral, transdermal or transmucosal administration; as well as parenteral delivery, including intramuscular, subcutaneous, intramedullary, intrathecal, intraventricular, intravenous, intraperitoneal, or intranasal administration. For injection, the pharmaceutical compositions of the disclosure may be formulated in aqueous solutions, for example, in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The compounds of the disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. For topical use, creams, ointments, jellies, solutions or suspensions, etc., containing the compounds of the disclosure are employed. For purposes of this application, topical application shall include mouthwashes and gargles.

The compounds of the disclosure may also be administered to the patient utilizing transdermal patch devices, optionally with other delivery systems. Transdermals include all the various types known in the art including, reservoir, matrix, gel including hydrogel, and non-woven.

In the methods described herein, an appropriate dosage level will generally be about 0.01 to 500 mg per kg patient body weight per day which can be administered in single or multiple doses. The dosage level can be about 0.01 to about 250 mg/kg per day, such as 0.01 to about 100 mg/kg per day, for example, 0.01 to about 10 mg/kg per day, such as 0.04 to about 5 mg/kg per day, or about 0.5 to about 100 mg/kg per day. A suitable dosage level may be also about 0.05 to 100 mg/kg per day, or about 0.1 to 50 mg/kg per day or 1.0 mg/kg per day. Within this range the dosage may be 0.05 to 0.5, 0.5 to 5 or 5 to 50 mg/kg per day for example. The Examples section shows that one of the exemplary compounds was dosed at 0.1 mg/kg/day while another was effective at about 1.0 mg/kg/day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or once or twice per day. There may be a period of no administration followed by another regimen of administration. Administration of the compounds may be closely associated with the schedule of a second agent of administration.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The cholinergic system is targeted by several drugs used to treat neural disorders such as Parkinson's disease. There is a well-documented inverse correlation between smoking and PD, and other disorders that can be treated with dopamine (DA) drugs (ADHD, schizophrenia) are associated with a high incidence of smoking. These findings suggest the important role played by the cholinergic system in DA transmission.

Specific agonists or antagonists may, by targeting endogenous cholinergic mechanisms, provide a new method for manipulating DA transmission in neurological diseases such as Parkinson's disease, nicotine dependence, or attention deficit hyperactivity disorder (ADHD).

Nitric oxide (NO) is an endogenous neurotoxin. Though NO is commonly used by the nervous system in inter-neuron communication and signaling, it can be active in mechanisms leading to ischemia in the cerebrum. The neurotoxicity of NO is based on its importance in glutamate excitotoxicity, as NO is generated in a calcium-dependent manner in response to glutamate mediated NMDA activation, which occurs at an elevated rate in glutamate excitotoxicity. Though NO facilitates increased blood flow to potentially ischemic regions of the brain, it is also capable of increasing oxidative stress, inducing DNA damage and apoptosis. Thus, an increased presence of NO in an ischemic area of the CNS can produce significantly toxic effects.

Guggulsterone [4,17(20)-pregnadiene-3,16-dione] is a plant sterol derived from the gum resin (guggulu) of the tree *Commiphora mukul* and exists as both E- and Z-isomers. Methods for separating E- and Z-isomers of alkenes, including E-guggulsterone and Z-guggulsterone are known in the art. The resin has been used in Ayurvedic medicine for centuries to treat a variety of ailments, including obesity, bone fractures, arthritis, inflammation, cardiovascular disease and lipid disorders. The effectiveness of guggul for treating osteoarthritis of the knee also has been demonstrated. Recent studies have shown that guggulsterone is an antagonist for the bile acid receptor farnesoid X receptor. Other studies have shown that guggulsterone enhances transcription of the bile salt export pump, thereby regulating cholesterol homeostasis. An understanding of the molecular mechanisms underlying guggulsterone is just now emerging. It has been shown that guggulsterone can suppress inflammation by inhibiting inducible nitric oxide synthetase (iNOS) expression induced by lipopolysaccharide in macrophages.

Kynurenic acid (KYNA) (4-hydroxyquinoline-2-carboxylic acid) is a product of the normal metabolism of amino acid L-tryptophan. It has been shown that kynurenic acid possesses neuroactive activity. It acts as an antiexcitotoxic and anticonvulsant, most likely through acting as an antagonist at excitatory amino acid receptors. Because of this activity, it may influence important neurophysiologic and neuropathologic processes. As a result, kynurenic acid has been considered for use in therapy in certain neurobiological disorders. Conversely, increased levels of kynurenic acid have also been linked to certain pathological conditions.

A wealth of evidence exists to point to the principal involvement of GSK-3 in the processes of neuronal apoptosis and neurodegeneration. Examples range from the physiologically appropriate forms of apoptosis that occur during development to the undesirable tissue damage that results from strokes and other instances of ischemia. The implications of pharmacological manipulation of such events for human health is manifest in the association of lithium therapy with an increase in the volume grey matter in bipolar patients, an effect linked to the neuroprotective properties of lithium.

During development, appropriate target innervation is partially governed by matching a trophic factor in the target with its receptors on in-growing afferent fibers. Thus, a neuron sending its primary process into an inappropriate target field will become starved for its preferred trophic factor, and the neuron will die, qualitatively eliminating an inappropriate connection. Similarly, excessive in-growth to a target can be regulated quantitatively by competition between the arriving fibers for a limited supply of trophic factor. These events are modeled in cell culture through the removal of a trophic factor from a neuronal culture that depends on said factor for viability. With respect to the Wnt signaling pathway, it is rather obvious that sufficient supplies of ligand would suppress GSK-3 and its phosphorylation of β-catenin, thereby freeing β-catenin from degradation and allowing it to influence the transcription of genes. β-catenin appears to generally enhance transcription of prosurvival genes and inhibit the expression of apoptotic genes. The dominant role of GSK-3 in neuronal cell death has been demonstrated though overexpression of GSK-3β in a human neuroblastoma cell line, which sensitized these cells to the proapoptotic effects of staurosporine or heat shock. Similarly, similar overexpression of GSK-3β in vivo results in frank neurodegeneration.

Kenpaullone (9-bromo-7,12-dihydro-indolo [3,2-d] [1]benzazepin-6(5H)-one) has been shown to inhibit glycogen synthase kinase 3 (GSK-3β) and to increase β-catenin activity.

According to an embodiment of the invention, the disease or disorder is or involves a neurodegenerative disease or disorder (for example, a chronic neurodegenerative disease or disorder), such as non-viral encephalopathy, Alzheimer's disease, Parkinson's disease, ALS, Huntington disease, multiple sclerosis (MS) or rare genetic disease.

Preferably, the neurodegenerative disease or disorder is a non-viral disease or disorder, more preferably a non-bacterial and non-viral disease or disorder, still more preferably a non-microbial disorder.

According to an embodiment of the invention, the condition is or involves a neurodegenerative condition, such as aging. According to one embodiment of the invention, the disease, disorder or condition is or involves a physical or ischemic injury of the nervous system, such as seizure, stroke, trauma, epilepsy.

Although the invention has been described with reference to the above examples, it will be understood that modifications and variations are encompassed within the spirit and scope of the invention. Accordingly, the invention is limited only by the following claims.

What is claimed is:

1. A method for the treatment of Parkinson's disease (PD), consisting of administering to a subject in need thereof a therapeutically effective amount of a composition consisting of guggulsterone and a pharmaceutically acceptable carrier.

2. The method of claim 1, wherein guggulsterone is administered orally or by injection.

3. The method of claim 1, wherein guggulsterone is administered intravenously.

4. The method of claim 1, wherein guggulsterone is administered orally or by injection.

5. The method of claim 1, wherein guggulsterone is administered intravenously.

6. A method for modulating dopaminergic neuronal activity in a subject in need thereof, consisting of contacting dopaminergic neurons with a composition consisting of guggulsterone and a pharmaceutically acceptable carrier, thereby modulating dopaminergic neuronal activity.

7. The method of claim 6, wherein the dopaminergic neuronal activity is promoted or increased.

8. The method of claim 6, wherein the dopaminergic neuronal activity is neuron function, neuron survival, or neurite outgrowth.

9. The method of claim 6, wherein dopamine release is increased or stimulated.

10. A method for the treatment of Parkinson's disease (PD), consisting of administering to a subject in need thereof a therapeutically effective amount of a composition consisting of guggulsterone, kynurenic acid and a pharmaceutically acceptable carrier.

11. A method for the treatment of Parkinson's disease (PD), consisting of administering to a subject in need thereof a therapeutically effective amount of a composition consisting of guggulsterone, kenpaullone and a pharmaceutically acceptable carrier.

12. A method for modulating dopaminergic neuronal activity in a subject in need thereof, consisting of contacting dopaminergic neurons with a composition consisting of guggulsterone, and kynurenic acid and a pharmaceutically acceptable carrier, thereby modulating dopaminergic neuronal activity.

13. A method for modulating dopaminergic neuronal activity in a subject in need thereof, consisting of contacting dopaminergic neurons with a composition consisting of guggulsterone, kenpaullone and a pharmaceutically acceptable carrier, thereby modulating dopaminergic neuronal activity.

* * * * *